United States Patent [19]
Hilfman

[11] 3,931,048
[45] Jan. 6, 1976

[54] HYDROCARBON CONVERSION CATALYTIC COMPOSITE
[75] Inventor: Lee Hilfman, Mount Prospect, Ill.
[73] Assignee: Universal Oil Products Company, Des Plaines, Ill.
[22] Filed: May 3, 1974
[21] Appl. No.: 466,759

[52] U.S. Cl............... 252/455 R; 252/453; 208/111
[51] Int. Cl.² .................... B01J 29/06; C10G 13/02
[58] Field of Search.......... 252/453, 455 R; 208/111

[56] References Cited
UNITED STATES PATENTS

| | | | |
|---|---|---|---|
| 3,216,922 | 11/1965 | O'Hara | 208/111 |
| 3,433,748 | 3/1969 | Magee, Jr. et al. | 252/453 |
| 3,472,791 | 10/1969 | Vesely | 252/453 X |

Primary Examiner—Carl F. Dees
Attorney, Agent, or Firm—James R. Hoatson, Jr.; Thomas K. McBride; William H. Page, II

[57] ABSTRACT

A catalytic composite, comprising a combination of a nickel component and a tungsten component with a silica-alumina carrier material wherein said carrier material is co-gelled silica-alumina consisting of from about 43 percent to about 57 percent by weight of alumina and from about 57 percent to 43 percent by weight silica and wherein said components are present in amounts sufficient to result in the composite containing, on an elemental basis, about 2 to about 10 percent by weight of the nickel component and about 8 to about 20 percent by weight of the tungsten component, is disclosed. Key features of the subject composite are the criticality of the alumina content of the carrier material and the facility of using a co-gelled silica-alumina carrier material. The principal utility of the subject composite is in the hydrocracking of hydrocarbons. A specific example of the catalyst disclosed is a combination of nickel and tungsten with a co-gelled silica-alumina carrier material containing 50 weight percent alumina in amounts sufficient to result in the composite containing, on an elemental basis, about 7 to about 9 weight percent nickel and about 17 to about 19 weight percent tungsten.

3 Claims, 1 Drawing Figure

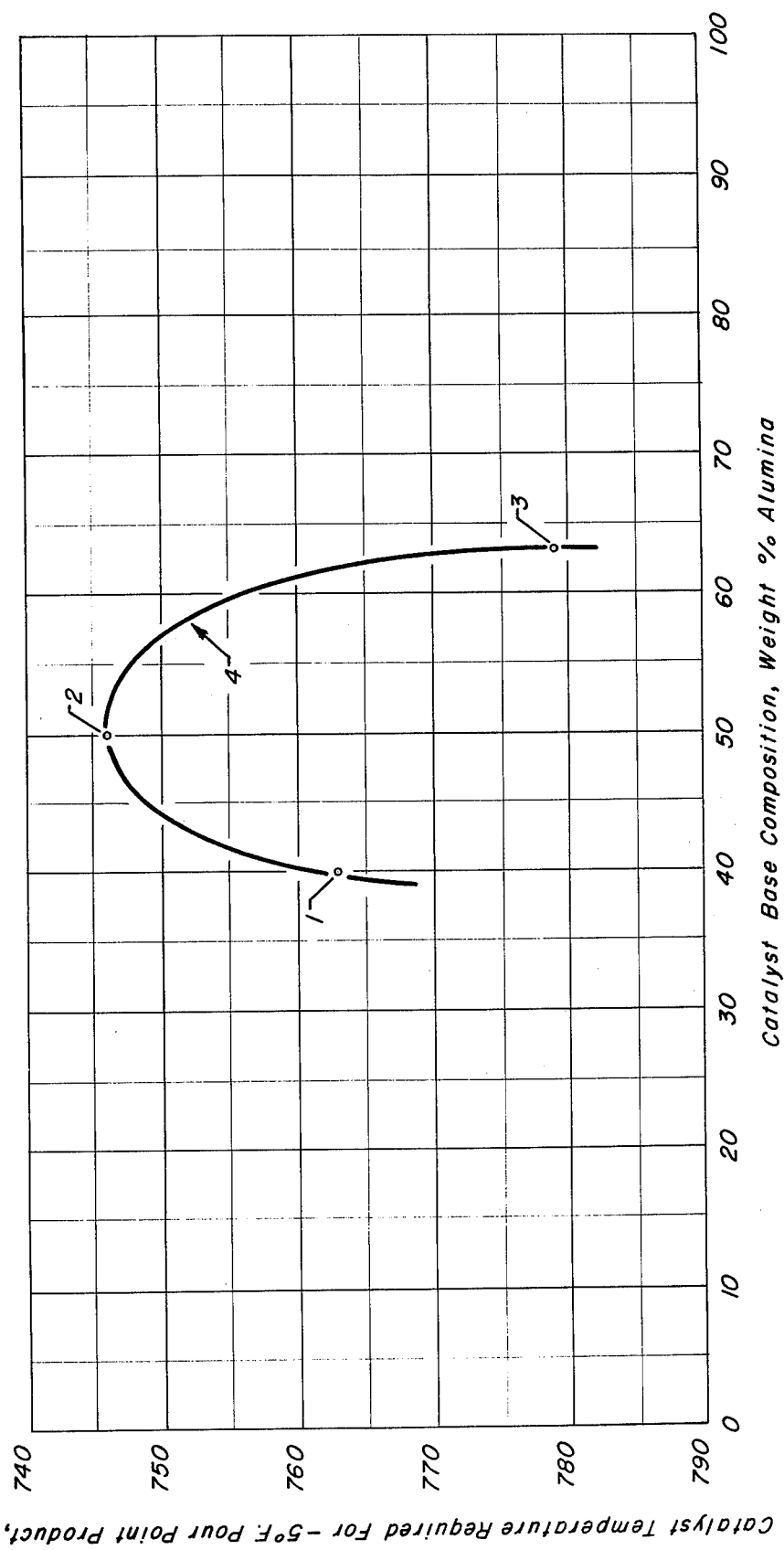

HYDROCARBON CONVERSION CATALYTIC COMPOSITE

The subject of the present invention is a novel catalytic composite which has exceptional activity, selectivity and resistance to deactivation when employed in a hydrocarbon conversion process. This invention also relates to the preparation of a novel catalytic composite. More particularly, the invention relates to a catalyst which is useful for performing destructive hydrogenation of hydrocracking of hydrocarbons.

Destructive hydrogenation by catalytic means, more commonly called hydrocracking, is old and well-known to the art. Destructive hydrogenation of the hydrocarbon oil, which is usually a coal tar or a high-boiling petroleum fraction, such as gas oils or topped crude, generally is performed at relatively high temperatures and pressures of the order of 750°F. and 1500 psig. and upward. Catalysts for the destructive hydrogenation of hydrocarbons are generally a combination of hydrogenation and cracking catalysts.

While many types of catalyst compositions have been proposed for destructive hydrogenation or hydrocracking, it has been found that catalysts comprised of silica, alumina, tungsten and nickel are especially suitable. Such catalysts are well known in the hydrocracking art.

From U.S. Pat. No. 3,216,922, a process is known for the preparation of hydrocracking catalysts comprising a silica-alumina mixture as a carrier in which the carrier is obtained by first precipitating silica gel from a water glass solution and subsequently, after aging of the gel, precipitating aluminum hydroxide thereon. As the aluminum salt from which the aluminum hydroxide is formed, use is made of aluminum sulphate which is added in such a quantity that the molar ratio of silica to alumina in the finished carrier is approximately 5:1. It was found, however, that the use of hydrocracking catalysts, of which the carrier was obtained in the manner described, produced less favorable results in the hydrocracking of flashed distillates.

In an effort to prepare a more satisfactory hydrocracking catalyst, British Pat. No. 1,183,778 teaches a process for the preparation of an alumina-silica-nickel-tungsten hydrocracking catalyst which comprises preparing a catalyst carrier by first precipitating from an aqueous solution comprising silicate ions, a silica gel, subjecting the gel to aging at elevated temperature, precipitating aluminum hydroxide on the aged gel by addition of an aqueous aluminum nitrate solution and an alkaline-reacting solution, separating, drying and finally calcining the resulting precipitate of aluminum hydroxide on silica gel and then supporting tungsten and nickel on the catalyst carrier and subsequently oxidizing the carrier comprising the metal salts.

However, because commercial scale hydrocracking of hydrocarbons is performed at low space velocities, catalyst cost is an appreciable factor in both the initial investment and operating costs of hydrocracking plants. For this reason, there is considerable incentive to manufacture such catalysts by the most economic method while improving the catalyst activity. I have discovered an improved process for the preparation of tungsten-nickel on silica-alumina hydrocracking catalyst.

More specifically, I have found that a co-gelled silica-alumina is an exceptionally suitable carrier material. A co-gelled silica-alumina carrier material in addition to being catalytically suitable is more simply and economically produced than the prior art carriers. The production of prior art carriers has been a multi-step process which has required the expenditure of time and effort far in excess of that required for a co-gelled carrier.

More specifically, my process is an improved process for the preparation of such catalyst wherein the nickel component is present in an amount from about 2 weight percent to about 10 weight percent, and the tungsten component is present in an amount from about 8 weight percent to 20 weight percent. I have also discovered that an unusually superior catalyst results if the catalyst base contains from about 43 percent to about 57 percent by weight of alumina. The criticality of the range of the alumina concentration is further illustrated hereinbelow.

A particularly preferred co-gelled silica-alumina catalyst base comprises from about 43 percent to about 57 percent alumina and from about 57 percent to about 43 percent silica and still more preferably from about 48 percent to about 52 percent alumina.

In addition to the foregoing compositional limitations, it is important that the catalyst base have adequate pore volume, that is, a pore volume of at least 0.5 cc./g. and preferably at least 0.6 cc./g. or even 0.7 cc/g.

The co-gelled silica-alumina catalyst base is preferably in the xerogel state, that is, it is dried sufficiently to afford the usual microporous structure and therefore an appreciable available surface. It is also possible to use a rigid silica-alumina catalyst base which has merely been dried at a relatively low temperature, e.g., 125°C., and which still contains considerable amounts of water. In this latter case, however, the degree of drying must nevertheless be sufficient to remove essentially all water from the pores of the base.

The catalyst of the present invention can be utilized to achieve the maximum production of LPG (liquefied petroleum gas) in the propane/butane range from naphtha or gasoline boiling range distillates. Heavier charge stocks, including kerosenes, light gas oils, heavy gas oils, full boiling range gas oils and "black oils" may be readily converted into lower-boiling, normally liquid products including gasolines, kerosenes, middle-distillates, lube oils, etc.

In one embodiment accordingly, the present invention provides a method of preparing catalysts having hydrocracking activity comprising the steps: (a) co-gelling a silica-alumina carrier material consisting of from about 43 percent to about 57 percent by weight alumina and from about 57 to 43 percent by weight silica; (b) impregnating said silica-alumina carrier material with an aqueous solution of a nickel salt and a tungsten salt, the concentrations of the salts in the aqueous solution being sufficient to deposit on the carrier material an amount of salts equivalent to 2 to 10 percent by weight nickel and 8 to 20 percent by weight tungsten based on the total weight of the finished catalyst; and, (c) calcining the impregnated carrier material.

In a second embodiment, the present invention relates to a process for hydrocracking hydrocarbons which process comprises reacting said hydrocarbons with hydrogen in a reaction zone containing a catalytic composite prepared by a method comprising the steps: (a) co-gelling a silica-alumina carrier material consisting of from about 43 percent to about 57 percent by weight alumina and from about 57 to 43 percent by weight silica; (b) impregnating said silica-alumina carrier material with an aqueous solution of a nickel salt and a tungsten salt, the concentrations of the salts in the aqueous solution being sufficient to deposit on the carrier material an amount of salts equivalent to 2 to 10 percent by weight nickel and 8 to 20 percent by weight tungsten based on the total weight of the finished catalyst; and, (c) calcining the impregnated carrier material.

In a specific embodiment, the hydrocracking conditions include a maximum catalyst bed temperature of about 600°F. to about 900°F., a pressure of about 500 to about 5,000 psig., a liquid hourly space velocity of about 0.1 to about 10 and a hydrogen circulation rate in the range of about 1,000 to about 50,000 scf./bbl.

In another specific embodiment, the catalytic composite is oxidized, in an atmosphere of air, at a temperature about 1,000°F. prior to contact with the fresh feed charge stock.

Another embodiment relates to a catalytic composite, comprising a combination of a nickel component and a tungsten component with a silica-alumina carrier material wherein said carrier material is co-gelled silica-alumina consisting of from about 43 percent to about 57 percent by weight alumina and from about 57 percent to 43 percent by weight silica and wherein said components are present in amounts sufficient to result in the composite containing, on an elemental basis, about 2 to about 10 percent by weight of the nickel component and about 8 to about 20 percent by weight of the tungsten component.

Other objects and embodiments of my invention relate to additional details regarding the preferred catalytic ingredients, the concentration of components within the catalytic composite, the method of catalyst preparation, preferred processing techniques and similar particulars which are hereinafter set forth.

Catalytic composites, tailored for the conversion of hydrocarbonaceous material and particularly those intended for utilization in a hydrocracking process, have traditionally consisted of metallic elements chosen from Group VIII of the Periodic Table; however, metallic components from Group VI-B are quite often incorporated therein. In those instances where hydrocracking is intended to be accompanied by some hydrorefining (desulfurization, denitrification, etc.) the preferred metallic components have been nickel and molybdenum, and nickel and tungsten, which components are usually combined with a porous carrier material comprising both alumina and silica, either amorphous or zeolitic in nature. Ample evidence may be found in the literature which confirms the ability of the nickel component to effect both cracking and hydrogenation reactions. Furthermore, the prior art indicates a preference for two particular methods of catalyst preparation. Predominantly preferred is an impregnating procedure wherein a previously calcined, preformed carrier material, which is precipitated in a multi-step manner as hereinabove described, is contacted with suitable soluble compounds of the nickel component and the Group VI-B component, where the latter is utilized. Impregnation involves both subsequent drying at a temperature of about 300°F., and oxidation at a temperature of about 1,100°F. The second preferred preparation scheme involves coprecipitating all the catalyst components, including those of the carrier material.

I have found that a particularly effective silica-alumina-nickel-tungsten hydrocracking catalyst can be prepared when the alumina content of the co-gelled silica-alumina support is maintained within the critical range of from about 43 percent to about 57 percent by weight alumina. Thus, it is now possible to prepare a more active and stable hydrocracking catalyst.

As is customary in the art of catalysis, when referring to the catalytically active metal, or metals, it is intended to encompass the existence of such metal in the elemental state or in some form such as an oxide, sulfide, halide, etc. Regardless of the state in which the metallic components actually exist, the concentrations are computed as if they existed in the elemental state.

The co-gelled silica-alumina may be prepared and utilized as spheres, pills, pellets, extrudates, granules, etc. In a preferred method of manufacture, an aqueous water glass solution, diluted to a silica concentration of from about 5 to about 15 weight percent, is acidified with hydrochloric acid or other suitable mineral acid. The resulting sol is acid aged at a pH of from about 4 to about 4.8 to form a hydrogel, and the hydrogel is further aged at a pH of from about 6.5 to about 7.5. The silica hydrogel is then thoroughly admixed with an aqueous aluminum salt solution of sufficient concentration to provide a desirable alumina content in the silica-alumina product. The silica-alumina sol is then precipitated at a pH of about 8 by the addition of a basic precipitating agent, suitably aqueous ammonium hydroxide. The silica-alumina, which exists as a hydrogel slurried in a mother liquor, is recovered by filtration, water-washed and dried at a temperature of from about 200° to about 500°F. Drying is preferably by spray-drying techniques whereby the co-gelled silica-alumina is recovered as microspheres, admixed with a suitable binding agent, such as graphite, polyvinyl alcohol, etc., and extruded or otherwise compressed into pills or pellets or uniform size and shape.

The particularly preferred method for preparing the co-gelled silica-alumina support is by the well known oil-drop method which permits the utilization of the support in the form of macrospheres. For example, an alumina sol, utilized as an alumina source, is commingled with an acidified water glass solution as a silica source, and the mixture further commingled with a suitable gelling agent, for example, urea, hexamethylenetetramine, or mixtures thereof. The mixture is discharged while still below gellation temperature, and by means of a nozzle or rotating disk, into a hot oil bath maintained at gellation temperature. The mixture is dispersed into the oil bath as droplets which form into spheriodal gel particles during passage therethrough. The alumina sol is preferably prepared by a method wherein aluminum pellets are commingled with a quantity of treated or deionized water, with hydrochloric acid being added thereto in a sufficient amount to digest a portion of the aluminum metal and form the desired sol. A suitable reaction rate is effected at about reflux temperature of the mixture.

The spheroidal gel particles prepared by the oil-drop method are aged, usually in the oil bath, for a period of at least 10–16 hours, and then in a suitable alkaline or basic medium for at least 3 to about 10 hours, and finally waterwashed. Proper gellation of the mixture in the oil bath, as well as subsequent aging of the gel spheres, is not readily accomplished below about 120°F., and at about 210°F., the rapid evolution of the gases tends to rupture and otherwise weaken the spheres. By maintaining sufficient superatmospheric pressure during the forming and aging steps in order to maintain water in the liquid phase, a higher temperature can be employed, frequently with improved results. IF the gel particles are aged at superatmospheric pressure, no alkaline aging step is required.

The spheres are water-washed, preferably with water containing a small amount of ammonium hydroxide and/or ammonium nitrate. After washing, the spheres are dried, at a temperature of from about 200°F. to about 600°F. for a period of from about 6 to about 24 hours or more, and then calcined at a temperature of from about 800° to about 1,400°F. for a period of from about 2 to about 12 hours or more.

The nickel component and the tungsten component are composited with the co-gelled silica-alumina carrier material by any suitable co-impregnation technique. Thus, the carrier material can be soaked, dipped, suspended, or otherwise immersed in an aqueous impregnating solution containing a soluble nickel salt and a soluble tungsten salt. One suitable method comprises immersing the carrier material in the impregnating solution and evaporating the same to dryness in a rotary steam dryer, the concentration of the impregnating solution being such as to ensure a final catalyst composite comprising from about 2 to about 10 percent by weight nickel and 8 to about 20 percent by weight tungsten.

The catalyst composite is usually dried at a temperature of from about 200° to about 500°F. for a period of from about 1 to about 10 hours prior to calcination. In accordance with the present invention, calcination is effected in an oxidizing atmosphere at a temperature of from about 700° to about 1,200°F. The oxidizing atmosphere is suitably air, although other gases comprising molecular oxygen may be employed.

Following the high temperature oxidation procedure the catalyst is usually reduced for a period of from about ½ to about 10 hours at a temperature in the range of from about 700°F. to about 1,000°F. in the presence of hydrogen. The catalyst may be used in a sulfided form. Thus after reduction, the catalyst may be subjected to sulfidation by passing hydrogen sulfide, or other suitable sulfur containing compound, in contact therewith, preferably at an elevated temperature of from about 500°F. to about 1,100°F. The reduced catalyst is preferebly sulfided by contacting the catalyst with a stream of hydrogen containing from about 1 to 20 percent or more by volume of hydrogen sulfide at elevated temperatures of from about 500°F. to about 1,100°F. When the petroleum hydrocarbon to be hydrocracked contains sulfur compounds, by design or otherwise, sulfidation may be suitably effected in situ in the initial stages of the hydrocracking process.

The catalyst composite, prepared in accordance with the method of this invention, is preferably employed in a reaction zone as a fixed bed. The hydrocarbon charge stock after being combined with hydrogen in an amount of from about 2,000 to about 20,000 standard cubic feet per barrel, and preferably at least about 5,000 standard cubic feet per barrel, is introduced into the reaction zone. THe charge stock may be in a liquid, vapor, or liquid-vapor phase mixture, depending upon the temperature, pressure, proportion of hydrogen and the boiling range of the charge stock being processed. The liquid hourly space velocity through the reaction zone will be in excess of about 0.2 and generally in the range of from about 1.0 to about 15.0. The source of hydrogen being admixed with a hydrocarbon charge stock may comprise a hydrogen-rich gas stream which is withdrawn from a high-pressure, low-temperature separation zone and recycled to supply at least a portion of such hydrogen. Excess hydrogen resulting from the various dehydrogenation reactions effected in a catalytic reforming unit may also be employed in admixture with the hydrocarbon charge. The reaction zone will operate under an imposed pressure within the range of from about 80 to about 3,000 pounds per square inch gauge. The catalyst bed inlet temperature is maintained within the range of from about 350° to about 800°F. Since the hydrocracking reactions are exothermic, the outlet temperature or the temperature at the bottom of the catalyst bed will be significantly higher than that at the inlet thereto. The degree of exothermicity exhibited by the temperature rise across the catalyst bed is at least partially dependent upon the character of the charge stock passing therethrough, the rate at which the normally liquid hydrocarbon charge contacts the catalyst bed, the intended degree of conversion to lower-boiling-hydrocarbon products, etc. In any event, the catalyst bed inlet temperature will be such that the exothermicity of the reactions taking place does not cause the temperature at the outlet of the bed to exceed about 900°F., and preferably 850°F. The operation may also be effected as a moving-bed type, or suspensoid type of operation in which the catalyst, hydrocarbon and hydrogen are admixed and passes as a slurry through the reaction zone.

Although the method of preparing the catalyst, and careful selection of operating conditions within the ranges hereinbefore set forth, extend the effective life of the catalyst composite, regeneration thereof may eventually become desired due to the natural deterioration of the catalytically active metallic components. The catalytic composite is readily regenerated by treating the same in an oxidizing atmosphere, at a temperature of from about 750° to about 850°F., and burning coke and other heavy hydrocarbonaceous material therefrom. The catalyst composite may then be subjected to the reducing action in hydrogen, in situ, at a temperature within the range of from about 1,000° to about 1,200°F. If desirable, the catalyst may then be sulfided in the same manner as fresh catalyst as hereinbefore described.

The drawing included in the instant application is for the purpose of visually demonstrating the improvements and advantages afforded by the manufacture of silica-alumina-nickel-tungsten hydrocracking catalyst according to the present invention.

The following example is presented in illustration of the catalyst of this invention and a method of preparation thereof, and is not intended as an undue limitation on the generally broad scope of the invention as set out in the appended claims.

EXAMPLE

This example describes the preparation and testing of three silica-alumina-nickel-tungsten catalysts each of which contains 8% nickel and 18% tungsten and which contain 40, 50 and 63 weight percent alumina, respectively. The co-gelled silica-alumina support material for each catalyst was prepared by the hereinabove described oil-drop method and the ratio of silica and alumina sources was selected to yield a finished support material which had the desired alumina content. The finished support material was in the form of 1/16 inch spheres.

A batch of co-gelled support material containing 40 weight percent alumina was impregnated with an aqueous solution of nickel nitrate and ammonium metatungstate. The impregnated spheres were dried and then oxidized at a temperature of 1,100°F. The concentration of the metal salts in the aqueous impregnation solution was selected to yield a finished catalyst which contained 8 weight percent nickel and 18 weight percent tungsten. This batch of finished hydrocracking catalyst will hereinafter be referred to as catalyst 1.

A batch of co-gelled support material containing 50 weight percent alumina was then used to prepare catalyst 2 in the same manner as catalyst 1. Catalyst 2 also contained 8 weight percent nickel and 18 weight percent tungsten.

A batch of co-gelled support material which contained 63 weight percent alumina was impregnated to yield a finished catalyst 3 containing 8 weight percent nickel and 18 weight percent tungsten in exactly the same manner as the two previous preparations.

Each of the catalysts prepared in this manner were then used in the hydrocracking of a light vacuum gas oil whose properties are summarized in Table I.

TABLE I

| Properties Of Light Vacuum Gas Oil | |
|---|---|
| API° Gravity at 60°F. | 36.7 |
| Specific Gravity at 60°F. | 0.8413 |
| Distillation, °F. | |
| IBP | 550 |
| 10 | 635 |
| 30 | 688 |
| 50 | 716 |
| 70 | 742 |
| 90 | 785 |
| E.P. | 856 |
| Total Sulfur, wt. % | 0.07 |
| Total Nitrogen, wt. % | 0.044 |
| Aromatics, Vol. % | 12.7 |
| Paraffins and Naphthenes, vol. % | 87.3 |
| Pour Point, °F. | 80 |

In each case, the light vacuum gas oil was processed with a reactor pressure of 2,000 psig., a liquid hourly space velocity of 1.0, a hydrogen circulation rate of 9,500 scf./bbl. and at a catalyst bed temperature which was required to yield a 315°F.+ product with a −5°F. pour point. Catalysts 1, 2 and 3 required catalyst temperature of 763°F., 754°F. and 779°F., respectively, to yield the desired product characteristics. These data are presented in tabular form in Table II and in graphical form in the accompanying drawing.

TABLE II

| Evaluation For Hydrocracking Activity | | | |
|---|---|---|---|
| Catalyst Identity | 1 | 2 | 3 |
| Alumina Concentration | 40 | 50 | 63 |

TABLE II-continued

| Evaluation For Hydrocracking Activity | | | |
|---|---|---|---|
| Catalyst Identity | 1 | 2 | 3 |
| Reactor Temperature Required For −5°F. Pour Point | 763 | 754 | 779 |

From the data presented in foregoing Table I and with reference to the accompanying drawing, itt will be seen that the three catalysts' increasing concentrations of alumina in the carrier material, the latter ranging from 40% to 63% by weight, did not produce normally liquid hydrocarbon products with improved pour point characteristics at the lowest catalyst bed temperature. This is clearly brought out upon comparing the results obtained through the use of catalysts 1, 2 and 3 which resulted in catalyst bed temperatures of 763°F., 754°F. and 779°F., respectively, for the desired product characteristics. Datum points 1, 2 and 3 in the drawing are representative of the results obtained with catalysts 1, 2 and 3, respectively. These data were employed in preparing curve 4 of the drawing, which curve clearly illustrates the criticality attached to an alumina concentration within the range of about 43% to about 57% by weight, in order to produce a liquid product with the desired characteristics at the lowest catalyst bed temperature. The additional economic advantages afforded through this particular result will be readily recognized by those possessing skill within the art of petroleum refining processes.

The foregoing specification and example clearly illustrate the improvements emcompassed by the present invention and the benefits to be afforded a process for the production of lowerboiling hydrocarbon products with improved pour point characteristics.

I claim as my invention:

1. A catalytic composite comprising a combination of a nickel component, and a tungsten component with a silica-alumina carrier material wherein said carrier material is co-gelled silica-alumina consisting of from about 43 percent to about 57 percent by weight alumina and from about 57 to 43 percent by weight silica and wherein said components are present in amounts sufficient to result in the composite containing, on an elemental basis, about 2 to about 10 percent by weight of the nickel component and about 8 to about 20 percent by weight of the tungsten component.

2. A catalytic composite as defined in claim 1 wherein said carrier material consists of 50 percent by weight of alumina and wherein said composite contains, on an elemental basis, about 7 to about 9 percent by weight of nickel and about 17 to about 19 percent by weight of tungsten.

3. A catalytic composite comprising a combination of the catalytic composite of claim 1 with a sulfur component in amounts sufficient to incorporate about 0.05 to about 1 weight percent sulfur, calculated on an elemental basis.

* * * * *